US00PP35761P2

(12) United States Plant Patent
Alff

(10) Patent No.: US PP35,761 P2
(45) Date of Patent: Apr. 16, 2024

(54) ***PENSTEMON* PLANT NAMED 'BALROCURP'**

(50) Latin Name: *Penstemon barbatus*
Varietal Denomination: Balrocurp

(71) Applicant: Ball Horticultural Company, West Chicago, IL (US)

(72) Inventor: Emily E. Alff, Royersford, PA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/368,445

(22) Filed: Sep. 14, 2023

(51) Int. Cl.
*A01H 5/02* (2018.01)
*A01H 6/68* (2018.01)

(52) U.S. Cl.
USPC ..... Plt./465

(58) Field of Classification Search
USPC ..... Plt./263.1, 465
See application file for complete search history.

*Primary Examiner* — Karen M Redden
(74) *Attorney, Agent, or Firm* — Audrey Charles

(57) ABSTRACT

A new and distinct cultivar of *Penstemon* plant named 'Balrocurp', characterized by its deep purple-colored flowers with a white throat, dark green-colored foliage, and moderately vigorous, compact-upright growth habit, is disclosed.

1 Drawing Sheet

Latin name of genus and species of plant claimed: *Penstemon barbatus*.
Variety denomination: 'Balrocurp'.

BACKGROUND OF THE INVENTION

The present invention relates to a new and distinct cultivar of *Penstemon* plant botanically known as *Penstemon barbatus* and hereinafter referred to by the cultivar name 'Balrocurp'.

The new cultivar originated in a controlled breeding program in Cochranville, Pennsylvania during September 2015. The objective of the breeding program was the development of *Penstemon* cultivars having a long flowering season, large flowers, and a compact-upright growth habit suitable for borders and containers.

The new *Penstemon* cultivar is the result of cross-pollination. The female (seed) parent of the new cultivar is ROCK CANDY Purple 'Novapenpur', U.S. Plant Pat. No. 27,316, characterized by its dark purple-colored flowers with a white throat, medium green-colored foliage, and moderately vigorous, compact-upright growth habit. The male (pollen) parent of the new cultivar is ROCK CANDY Ruby 'Novapenrub', U.S. Plant Pat. No. 27,820, characterized by its dark pink-colored flowers with a white throat area, medium green-colored foliage, and moderately vigorous, compact-upright growth habit. The new cultivar was discovered and selected as a single flowering plant within the progeny of the above stated cross-pollination during September 2017 in a controlled environment in Cochranville, Pennsylvania.

Asexual reproduction of the new cultivar by terminal stem cuttings since September 2017 in Cochranville, Pennsylvania and Elburn, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balrocurp' as a new and distinct cultivar of *Penstemon* plant:

1. Deep purple-colored flowers with a white throat;
2. Dark green-colored foliage; and
3. Moderately vigorous, compact-upright growth habit.

Plants of the new cultivar differ from plants of the female parent primarily in having a deeper purple colored flowers and more branches per plant. Plants of the new cultivar differ from plants of the male parent primarily in having deep purple-colored flowers unlike the dark pink-colored flowers of the male parent.

Of the many commercially available *Penstemon* cultivars, the most similar in comparison to the new cultivar is ROCK CANDY Blue 'Novapenblu', U.S. Plant Pat. No. 27,786. However, in side-by-side comparison, plants of the new cultivar differ from plants of 'Novapenblu s' in at least the following characteristics:

1. Plants of the new cultivar have a deep purple flower color that is different from the bluish-purple flower color of plants of 'Novapenblu';
2. Plants of the new cultivar have larger diameter flowers than plants of 'Novapenblu'; and
3. Plants of the new cultivar have larger sepals than plants of 'Novapenblu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balrocurp'. The plants were approximately four months old and grown three plants per pot in 2.5-quart containers for approximately two months in an outdoor nursery environment in West Chicago, Illinois. Plants were given one pinch approximately one week after transplant.

DETAILED BOTANICAL DESCRIPTION

Figure 1:
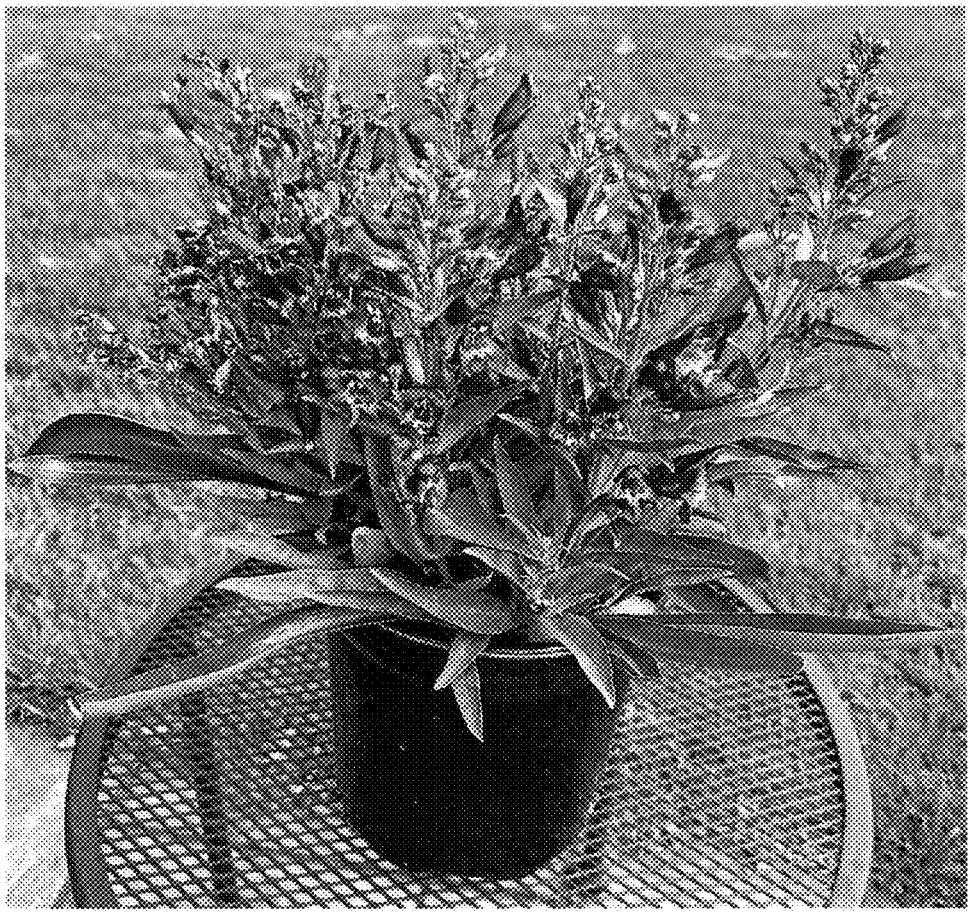
FIG. 1 illustrates a side view of the overall growth and flowering habit of 'Balrocurp'.
Figure 2:
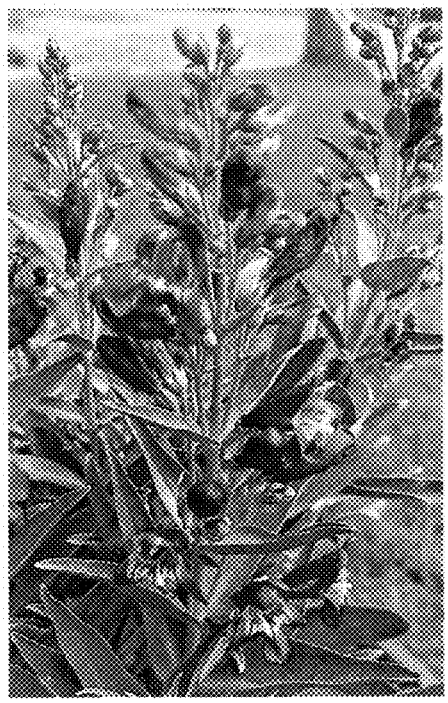
FIG. 2 illustrates a close-up view of an inflorescence of 'Balrocurp'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2023 under natural light conditions in Naperville, Illinois.

The following descriptions and measurements describe approximately four-month old plants produced from cuttings from stock plants and grown in a polycarbonate-covered greenhouse under conditions comparable to those used in commercial practice. Approximately six weeks after sticking, rooted plants were transplanted three plants per 2.5-quart container utilizing a soilless growth medium and grown for four weeks. Plants were then transferred to an outdoor nursery environment in West Chicago, Illinois and grown for approximately two months. Plants were given one pinch approximately one week after transplant. Prior to transferring outdoors, plants were grown in a polycarbonate greenhouse in West Chicago, Illinois. Greenhouse temperatures were maintained at approximately 70° F. to 75° F. (21.1° C. to 23.9° C.) during the day and approximately 60° F. to 65° F. (15.6° C. to 18.3° C.) during the night. Supplemental lighting was used. Measurements and numerical values represent averages of typical plants.

Botanical classification: *Penstemon barbatus* 'Balrocurp'.

Parentage:

*Female parent.*—ROCK CANDY Purple 'Novapenpur', U.S. Plant Pat. No. 27,316.

*Male parent.*—ROCK CANDY Ruby 'Novapenrub', U.S. Plant Pat. No. 27,820.

Propagation:

*Type cutting.*—Terminal stem.

*Time to initiate roots.*—Approximately 10 to 12 days.

*Time to produce a rooted cutting.*—Approximately 5 to 6 weeks.

*Root description.*—Fine to medium, fibrous.

*Rooting habit.*—Freely branching.

Plant description:

*Commercial crop time.*—Approximately 10 to 12 weeks from a rooted cutting to finish in a 15 cm container.

*Growth habit and general appearance.*—Herbaceous perennial; moderately vigorous, upright-compact growth habit.

*Hardiness.*—USDA Zone 5a (−20° F. to −15 F/−28.9° C. to −26.1° C.).

*Size.*—Height from soil level to top of plant plane: Approximately 23.0 cm. Width: Approximately 25.0 cm.

*Branching habit.*—Freely branching, pinching enhances lateral branching. Quantity of branches per plant: 5.

*Lateral branch.*—Shape: Round in cross section. Strength: Strong, flexible. Length to base of peduncle: Approximately 4.0 cm to 6.0 cm. Diameter: Approximately 4.0 mm. Length of central internode: Approximately 2.5 cm. Texture: Glabrous. Color of young and mature stem: 144A.

Foliage description:

*General Description.*—Quantity of leaves per branch: Approximately 10. Fragrance: None detected. Form: Simple. Arrangement: Opposite and decussate.

*Leaves.*—Aspect: Acute angle to stem. Shape: Lanceolate, keeled. Margin: Entire. Apex: Acute. Base: Sessile. Venation pattern: Pinnate. Length of mature leaf: Approximately 15.5 cm. Width of mature leaf: Approximately 1.5 cm to 2.5 cm. Texture of upper and lower surfaces: Glabrous. Color of upper surface of young and mature foliage: NN137A with midvein of 146C. Color of lower surface of young and mature foliage: NN137C with midvein of 146D.

Flowering description:

*Flowering habit.*—'Balrocurp' is a long-day obligate, freely flowering under outdoor growing conditions blooming from spring through autumn.

*Lastingness of individual floret.*—Approximately 5 to 7 days.

Inflorescence description:

*General description.*—Type: Terminal raceme, not persistent, multilateral symmetry. Quantity of open inflorescences per plant: Approximately 3. Fragrance: None detected. Length or height of inflorescence: Approximately 13.5 cm to 16.0 cm. Width of inflorescence: Approximately 7.0 cm. Quantity of fully-open flowers per inflorescence: Approximately 7.

*Peduncle.*—Strength: Strong. Aspect: Erect. Length: Approximately 3.0 cm. Diameter: Approximately 3.0 mm. Texture: Glabrous. Color: 144A.

Flower description:

*Type.*—Single, zygomorphic.

*Bud.*—Rate of opening: Generally takes 3 to 4 days for bud to progress from first color to fully open flower.

*Bud just before opening.*—Shape: Obovoid. Length: Approximately 2.6 cm. Diameter: Approximately 9.0 mm. Texture: Glabrous. Color: 77A.

*Corolla.*—Shape: Bilabiate, upper lip of two lobes and lower lip having three lobes. Width: Approximately 1.8 cm. Length: Approximately 2.1 cm. Depth: Approximately 3.0 cm.

*Upper lip lobes.*—Shape: Ovate. Margin: Entire. Apex: Rounded. Length from throat: Approximately 1.0 cm. Width: Approximately 7.0 mm. Texture of upper (inner) surface: Glabrous. Texture of lower (outer) surface: Glabrous. Color of upper (inner) surface when first and fully open: 77A. Color of lower (outer) surface when first and fully open: 77A with 79B.

*Lower lip lobes.*—Shape: Oblong. Margin: Entire. Apex: Rounded. Length from throat: Approximately 9.0 mm. Width: Approximately 5.0 mm. Texture of upper (inner) surface: Sparsely pubescent. Texture of lower (outer) surface: Glabrous. Color of upper (inner) surface when first and fully open: 77A with nectar guides of NN155A. Color of lower (outer) surface when first and fully open: 77A.

*Corolla tube.*—Length: Approximately 2.0 cm. Width: Approximately 9.0 mm. Texture of inner and outer surfaces: Glabrous. Color of inner surface: NN155D with stripes of 77A. Color of outer surface: 77A.

*Calyx.*—Shape: Overlapped sepals forming a cup shape. Length: Approximately 7.0 mm. Diameter: Approximately 4.0 mm.

*Sepals.*—Quantity per flower: 5. Apex: Acute. Base: Truncate. Length: Approximately 7.0 mm. Width: Approximately 3.0 mm. Texture of inner and outer surfaces: Glabrous. Color of inner surface: 144A. Color of outer surface: 144A with 137B.

*Pedicel.*—Strength: Strong, flexible. Aspect: At an acute angle. Length: Approximately 1.0 cm. Diameter: Approximately 1.0 mm. Texture: Glabrous. Color: 144A.

*Reproductive organs.*—Androecium: Stamen quantity: 5 per flower, one staminode, lacking a mature anther. Stamen length: Approximately 2.3 cm to 2.5 cm. Filament color: NN155D faintly tinted with 77A. Anther shape: Divergent. Anther length: Approximately 3.0 mm. Anther color: 158C. Pollen amount: Abundant. Pollen color: NN155D. Gynoecium: Pistil quantity: 1 per flower. Pistil length: Approximately 2.2 cm. Stigma shape: Conical. Stigma length: Less than 1.0 mm. Stigma color: NN155D. Style length: Approximately 1.8 cm. Style color: NN155D tinted with 77A. Ovary length: Approximately 4.0 mm. Ovary color: 144B.

Seed and fruit production: Neither seed nor fruit production has been observed.

Disease and pest resistance: Resistance to pathogens and pests common to *Penstemon* has not been observed.

What is claimed is:

1. A new and distinct cultivar of *Penstemon* plant named 'Balrocurp', substantially as herein illustrated and described.

* * * * *